United States Patent [19]

Giudicelli et al.

[11] 4,021,559

[45] May 3, 1977

[54] METHOD FOR TREATING SICKLE-CELL ANEMIA

[75] Inventors: Don Pierre René Lucien Giudicelli, Fontenay-sous-Bois; Henry Najer, Paris, both of France

[73] Assignee: Synthelabo, Paris, France

[22] Filed: Dec. 30, 1974

[21] Appl. No.: 537,379

[52] U.S. Cl. .................................. 424/262; 424/281
[51] Int. Cl.² ................ A61K 31/475; A61K 31/37
[58] Field of Search ................... 424/281, 256, 262

[56] References Cited
UNITED STATES PATENTS 3,438,988   4/1969   Giudicelli .......................... 260/253

OTHER PUBLICATIONS

Raper, *Ann. Soc. Belge Med Trop.*, pp. 205–210, 1969, 49 2.

Nouvelle Revue Française D'Hématologie, 1973, vol. 13, No. 2, pp. 274–277.

*Primary Examiner*—Frederick E. Waddell
*Attorney, Agent, or Firm*—Stevens, Davis, Miller & Mosher

[57] ABSTRACT

The invention provides a new method for treating sickle-cell anemia, by administering to an affected patient the vincamine salt of 6,7-dihydroxycoumarin-4-methylsulphonic acid.

3 Claims, No Drawings

METHOD FOR TREATING SICKLE-CELL ANEMIA

The invention relates to the treatment of sickle-cell anemia. It provides a new method for treating a patient suffering from this disease, which comprises administering to the said patient the vincamine salt of 6,7-dihydroxycoumarin-4-methylsulphonic acid. This compound has been described in U.S. Pat. No. 3,438,988, issued Apr. 15, 1969.

Sickle-cell anemia is a genotypical disease characterized by periodic crises. Presently, there is no specific treatment for it. And, till recently, it was even difficult to give the affected patients true remissions. The currently used drug was urea, but it is badly tolerated.

Since 1972, following clinical studies made at the assignee's instigation, it is known that the alkaloid vincamine itself gives very good results in the sickle-cell anemia patients. (see : Société Française d'Hématologie, Abidjan meeting, held on Nov. 23$^{rd}$ 1972, in Nouvelle Revue Française d'Hématologie, 1973, Vol. 13, No. 2, p. 274–277).

Vincamine may act as a curative drug, which shortens the sickle-cell anemia crises, or as a preventive drug. These actions are supposed to be based on its vasodilating activity and its oxygenating potency.

Unexpectedly, new researches have shown that the vincamine salt of 6,7-dihydroxycoumarin-4-methyl-sulphonic acid (hereinafter called Compound I) is more active, at lower doses, than vincamine (hereinafter called Compound II) contained in said salt. Moreover, the salt is less toxic than the alkaloid itself.

The present disclosure will give the results of
1. the toxicity tests on mice,
2. "in vitro" tests, performed on the blood of sickle-cell anemia patients,
3. one clinical trial.

The toxicity was studied on albino mice of the Ardenay stock, bred in the Centre National de la Recherche Scientifique breeding Center. Compound I and Compound II were orally, intravenously and intraperitonally administered. The L D 50 were graphically determined. The results are shown in Table I:

TABLE I

| COMPOUND | L D 50 (mg/kg of body-weight) | | |
|---|---|---|---|
| | Oral | I.V. | I.P. |
| Compound I | 3,000 | 148 | 640 |
| Compound II | 460 | 95 | 215 |

It can be seen that both compounds possess little toxicity and that Compound I is even far less toxic than Compound II.

The activity of both compound was evaluated "in vitro" on the blood of sickle-cell anemia patients. The experiments were designed to show the prevention of sickle-cells' formation, the reversibility of the phenomenon and the gelification-time of Haemoglobin-5 (Hb-5), the abnormal form of Haemoglobin found in sickle-cell patients' blood.

The addition of one drop of solution (1 mg/100 ml) of Compound I or II in a dilution (1/20) of normally shaped red cells in their own plasma, prevents the formation of sickle-cells; if sickle-cells are used instead of normally-shaped ones, they resume the normal shape in less than five minutes. This proves the good activity of both compounds.

The effect on the gelification-time of Hb-S allows to differentiate between the compounds. The method used was that of Murayama (MURAYAMA, Clin. Chem. 1967, Vol. 13, p. 578–588 ; NALBANDIAN, HENRY, NICHOLS, CAMP and WOLF, U.S.A. N R C Report No 894 (1970)). The used dosage was 1 mg/100 ml for Compound I and 3 mg/100 ml for Compound II. The longer is the time of gelification the better is the activity of the compound under evaluates.

The results, expressed as means of the individual results, are shown in table II.

TABLE II

| Treatment | Number of bloods | Mean time | Relative time |
|---|---|---|---|
| None (controls) | 63 | 5 min 04 sec | 1 |
| Compound I | 60 | 11 min 51 sec | 2,3 |
| Compound II | 59 | 9 min 07 sec | 1,47 |

From the results of this test, it can be seen that Compound I is much more active than Compound II: in fact, the relative gelification-time after treatment with Compound I is almost twice the one after Compound II, in spite of the later being used in a concentration treble that of Compound I.

The clinical trial was effected on 80 African patients from Ivory Coast, most of them under 20 years old. They were all suffering from major sickle-cell disease; no patient suffered from a mere sickle-cell trait. Every one was affected with 1–2 crises a month, each lasting from 5 to 10 days.

The dosage of Compound I or Compound II was individually devised, depending, on one hand, on the severity and the duration of the crisis and on the other hand, on the age and weight of the patient and his tolerance. Normally children from 5 to 14 years old were given half the adult dosage and children from 2 to 5 a quarter of the adult dosage. The products were administered by intravenous and oral routes. Nurslings received preferably suppositories.

With both compounds the results were good, but they were unexpectedly better with Compound I than with Compound II.

At the beginning of a crisis, one of the tried compounds was intravenously administered every 3–4 hours, at the dosage of 15–25 mg each time for an adult patient (older than 14) until the subsiding of the crisis.

Under Compound I the crisis subsided quicker (9 to 12 hours) than with Compound II (2–3 days). For an adult patient (more than 14 years old) this means that, in average, the crisis subsided after 50–75 mg of intravenously administered Compound I and 100–150 mg of intravenously administered Compound II.

After the subsiding of the crisis, the patients received a permanent maintenance dosage of the orally administered compounds (20–40 mg per day of Compound I and 40–60 mg per day of Compound II, for adults).

Under this schedule, the number of relapses were less with Compound I than with Compound II. In six months relapses were seen
 in about 15 % of the patients on Compound I
 in about 40 % of the patients on Compound II.

During this maintenance period, it was observed than the preferable concentrations of the drugs in the blood of the patients was 1 mg per 100 ml for Compound I
3 mg per 100 ml for Compound II.

The gelification-time of the Hoemoglobin of the treated patients was studied as in the in vitro test. The results are shown in Table III:

TABLE III

| | Gelification-time seconds |
|---|---|
| Controls (Before treatment) | 433 – 442 |
| Patients treated with Compound I | 759 – 1831 |
| Patients treated with Compound II | 585 – 607 |

All these results and facts abundantly prove that Compound I is the choice drug for treating sickle-cell anemia crises and preventing them. No undesirable side actions were seen under the used dosage.

According to the present invention, Compound I may be administered via oral or parenteral route in the daily dosage of 10–100 mg.

In patients over 2 years old, for the treatment of a crisis, the vincamine salt of 6,7-dihydroxy-coumarin-4-methyl sulphonic acid is usually administered by intravenous route and the dosage goes up to 100 mg per day for an adult above 14, up to 50 mg per day for a child from 5 to 14 and up to 25 mg per day for a child from 2 to 5. The permanent maintenance treatment is usually oral and the dosage goes up to 50 mg per day for an adult above 14, up to 25 mg per day for a child from 5 to 14 and up to 12,5 mg per day for a child from 2 to 5.

In nurslings under 2 years old, the endorectal route is usually prefered. The children receive suppositories containing 10 mg of the active drug: 1–4 per day during a crisis and 1 a day for permanent maintenance treatment.

We claim:
1. A method for treating a patient suffering from sickle-cell anemia, which comprises administering to the said patient the vincamine salt of 6,7-dihydroxycoumarin-4-methylsulphonic acid in an effective amount.
2. A method for treating a patient suffering from sickle-cell anemia, which comprises administering to said patient the vincamine salt of 6,7-dihydroxycoumarin-4-methylsulfonic acid, via oral or parenteral route, in a daily dosage of 10 to 100 mg.
3. A method of claim 1, wherein said vincamine salt is administered via an endorectal route to a nursling.

* * * * *